United States Patent [19]

Korthoff

[11] Patent Number: 5,041,128

[45] Date of Patent: Aug. 20, 1991

[54] COMBINED SURGICAL NEEDLE-SUTURE DEVICE POSSESSING AN INTEGRATED SUTURE CUT-OFF FEATURE

[75] Inventor: Herbert W. Korthoff, Westport, Conn.

[73] Assignee: United States Sirgical Corporation, Norwalk, Conn.

[21] Appl. No.: 532,960

[22] Filed: Jun. 4, 1990

Related U.S. Application Data

[63] Continuation-in-part of Ser. No. 413,240, Sep. 27, 1989.

[51] Int. Cl.[5] .............................................. A61B 17/00
[52] U.S. Cl. ....................................... 606/224; 606/227
[58] Field of Search ................................ 606/222-227

[56] References Cited

U.S. PATENT DOCUMENTS

| | | | |
|---|---|---|---|
| 86,769 | 2/1869 | Marriott | 606/222 |
| 295,612 | 3/1884 | Bailey | 606/226 |
| 299,305 | 5/1884 | Weed | 606/225 |
| 887,476 | 1/1908 | Bach . | |
| 1,106,667 | 8/1914 | Minahan | 606/222 |
| 1,250,114 | 12/1917 | Bigelow et al. | 606/226 |
| 1,558,037 | 10/1925 | Morton | 606/224 |
| 1,591,021 | 7/1926 | Davis | 606/222 |
| 1,613,206 | 1/1927 | Souttar | 606/224 |
| 1,665,216 | 4/1928 | Morton et al. | 606/222 |
| 1,678,361 | 7/1928 | Shearon | 606/225 |
| 1,757,129 | 5/1930 | McClure | 606/226 |
| 1,960,117 | 5/1934 | Lydeard . | |
| 1,981,651 | 11/1934 | Logan | 606/224 |
| 2,022,234 | 11/1935 | Everett . | |
| 2,240,330 | 4/1941 | Flagg et al. | 606/225 |
| 2,302,986 | 11/1942 | Vollrath | 606/225 |
| 2,411,079 | 11/1946 | Baule | 606/224 |
| 2,802,468 | 8/1957 | Everett | 606/222 |
| 2,814,296 | 11/1957 | Everett . | |
| 2,910,983 | 11/1959 | Everett | 606/225 |
| 2,928,395 | 3/1959 | Forbes et al. | 606/224 |
| 3,311,110 | 3/1967 | Singerman et al. | 606/224 |
| 3,394,704 | 7/1968 | Dery | 606/224 |
| 3,416,534 | 12/1968 | Quinn . | |
| 3,799,169 | 3/1974 | Beroff et al. | 606/227 |
| 3,835,912 | 9/1974 | Kristensen et al. | 29/471 |
| 3,875,946 | 4/1975 | Duncan | 606/227 |
| 3,880,167 | 4/1975 | Hardwick | 606/225 |
| 3,890,975 | 6/1975 | McGregor | 606/227 |
| 3,910,282 | 10/1975 | Messer et al. | 606/225 |
| 3,918,455 | 11/1975 | Coplan | 606/225 |
| 3,924,630 | 12/1975 | Walldorg | 606/227 |
| 3,926,194 | 12/1975 | Greenberg et al. | 606/227 |
| 3,943,933 | 3/1976 | Gertzman | 606/227 |
| 3,949,756 | 4/1976 | Ace | 606/227 |
| 3,963,031 | 6/1976 | Hunter | 606/227 |
| 3,980,177 | 9/1976 | McGregor | 606/227 |
| 3,981,307 | 9/1976 | Borysko | 606/224 |
| 4,054,144 | 10/1977 | Hoffman et al. | 606/224 |
| 4,072,041 | 2/1978 | Hoffman et al. | 606/225 |
| 4,124,027 | 11/1978 | Boss | 606/226 |
| 4,127,133 | 11/1978 | Martinez | 606/224 |
| 4,169,477 | 10/1979 | Bokros . | |
| 4,359,053 | 11/1982 | Benjamin | 606/225 |
| 4,411,654 | 10/1983 | Boarini et al. | 604/165 |
| 4,596,728 | 6/1986 | Yang et al. | 428/36 |
| 4,624,879 | 11/1986 | Van Dijck et al. | 428/102 |
| 4,672,734 | 6/1987 | Kawada et al. | 29/517 |
| 4,792,336 | 12/1988 | Hlavaceh et al. | 606/228 |
| 4,799,483 | 1/1989 | Kraff | 606/223 |
| 4,805,292 | 2/1989 | Noguchi | 29/445 |
| 4,932,963 | 6/1990 | Ritter et al. | 606/224 |

FOREIGN PATENT DOCUMENTS 0358451 3/1990 European Pat. Off. .

OTHER PUBLICATIONS

Raychem Corporation Product specification RT-850 for Thermofit ™ Kynar Tubing dated Mar. 6, 1984.

*Primary Examiner*—Stephen C. Pellegrino
*Assistant Examiner*—Gary Jackson
*Attorney, Agent, or Firm*—Thomas R. Bremer; Peter G. Dilworth; Rocco S. Barrese

[57] ABSTRACT

Attachment of a surgical needle to a suture to provide a combined surgical needle-suture device employs a shrinkable tubing possessing a suture cutting edge. Separation of the needle from the suture can be achieved when desired by bringing the suture to bear under tension against the cutting edge of the tubing thereby severing the suture.

15 Claims, 4 Drawing Sheets

COMBINED SURGICAL NEEDLE-SUTURE DEVICE POSSESSING AN INTEGRATED SUTURE CUT-OFF FEATURE

CROSS REFERENCE TO RELATED APPLICATION

This application is a continuation-in-part of commonly assigned, copending U.S. patent application Ser. No. 413,240, filed Sept. 27, 1989, pending. This application also relates by subject matter to commonly assigned, copending U.S. patent application Ser. No. 317,948, filed Mar. 2, 1989, now U.S. Patent No. 4,932,963, entitled "Combined Surgical Needle-Suture Device Possessing an Integrated Suture Cut-Off Feature", the contents of which are incorporated by reference herein.

BACKGROUND OF THE INVENTION

The present invention relates to a method for attaching a surgical needle to a suture to provide a combined surgical needle-suture device possessing controlled suture release characteristics and, more particularly, to such a method in which a shrinkable tubing possessing a suture cutting edge is employed to secure the needle to the suture. At the time separation of the needle from the suture is desired, e.g., at the conclusion of the suturing operation, the suture can be made to bear against the cutting edge of the tubing under tension thereby causing the suture to be severed from the needle.

For many years, surgeons have employed needle-suture combinations in which a suture or ligature is attached to the shank end of a needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acids.

Needle-suture combinations fall into two general classes: standard, or non-detachable, needle attachment and removable, or detachable, needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture (for various suture sizes) are set forth in the *United States Pharmacopoeia* (USP). The *United States Pharmacopoeia* prescribes minimum individual pull-out forces and minimum average pull-out forces as measured for five needle-suture combinations. The minimum pull-out attachment set forth in the *United States Pharmacopoeia* are hereby incorporated by reference.

One typical method for securing a suture to a needle involves providing a cylindrical recess in the shank end of a needle and securing a suture therein. For example, U.S. Pat. No. 1,558,037 teaches the addition of a cement secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull-out valve of 3 to 26 ounces. Alternative detachable attachment methods include providing a weakened suture segment (U.S. Pat. No. 3,949,756), lubricant tipping the end of a suture to be inserted in the axial bore of a needle (U.S. Pat. No. 3,963,031) and pre-tensioning a suture that is swaged within an axial needle bore (U.S. Pat. No. 3,875,946). See also, U.S. Pat. Nos. 3,799,169; 3,880,167; 3,924,630; 3,926,194; 3,943,933; 3,981,307; 4,124,027; and, 4,127,133.

Another method for attaching a suture to a needle involves the use of tubing which is secured to the shank end of the needle and to the suture. For example, U.S. Pat. No. 1,613,206 describes the use of a tubing (preferably silver) which is secured to the shank end of a needle and to a ligature. It is suggested that the tube may be attached to the needle by pressure or soldering and to the ligature by pressure or cementing. It is also suggested that the shank of the needle be of reduced cross section and that the furthest extremity of the reduced diameter shank section be provided with a spike or point upon which the suture may be secured prior to tube application.

U.S. Pat. No. 2,240,330 describes a tubing attachment method whereby the tubing and suture are releasably secured to the needle. In particular, the needle and tubing are provided with cooperating catch and abutment means which are released one from the other by rotating the needle 90° relative to the tubing (or vice versa). The tubing is manufactured from spring-tempered carbon steel or chrome nickel steel and is secured to the suture by heating the tubing and then swaging to the suture.

U.S. Pat. No. 3,311,100 relates to a flexible composite suture having a tandem linkage. The needle is secured to a flexible suture leader manufactured from a readily sterilizable plastic such as nylon, linear polyethylene, isotactic polypropylene, polyester, silk or other proteinaceous material, e.g., by inserting and crimping the leader within an axial bore in the needle shank. The opposite end of the suture leader is crimped within a connector sleeve of a thin walled metal tubing, e.g., stainless steel. The opposite end of the tubing is crimped around a stiff suture, e.g., monofilament stainless steel.

U.S. Pat. No. 3,918,455 describes a needle-suture attachment wherein a hollow suture portion is secured to the shank end of a needle which is of reduced cross-section as compared to the remainder of the needle.

Additional patents which describe the use of tubing to effect suture-needle attachment include U.S. Pat. Nos. 4,672,734 (forming needle from U-shaped metal plate around suture), 4,359,053 (silicone tubing), 3,835,912 (laser welding of metal tube to needle), 2,814,296, 2,802,468 (chamfered tubing ends), b 2,302,986, 2,240,330, 1,981,651 (needle and tubing screw threaded), 1,960,117, and 1,591,021.

Numerous disadvantages exist with methods used heretofore to effect needle-suture attachment. For example, those methods which involve the formation and use of an axial bore in the shank end of the needle require the use of expensive hole forming equipment. Moreover, it is difficult to maintain the bore concentric with the center-line of the needle and to control the depth (and diameter) of the bore when drilling the needle shank, whether using conventional drilling equipment or laser drilling. Another disadvantage is the possibility that foreign substances may inadvertently or uncontrollably be introduced into the needle bore, e.g., oil used during drilling or silicone from the needle silconization process. Safeguards employed in an attempt to prevent the introduction of such foreign materials, e.g., water blocking during needle silconization, are inconvenient adding time, effort and cost to the needle production process.

Attachment processes which employ bored needle shanks also limit the range of materials from which needles may be fabricated in a cost effective fashion. For example, it is exceedingly difficult to drill Series 300 stainless steel (laser drilling is required) and, once drilled, it is difficult to swage Series 300 stainless steel in a consistent and reliable manner. For this reason, Series 300 stainless steel is not employed for the vast majority of needled suture products despite its advantageous combination of strength and ductility characteristics as compared to conventionally employed Series 400 stainless steel.

Additional disadvantages associated with needle-suture attachment methods which employ bored needle shanks include the weakness imparted to the bored section of the needle, particularly after swaging, and the attendant increased possibility that the needle will fracture in this region. It is also difficult to provide a specialized surface finish to the needle shank to assist in needle attachment, e.g., a texturized surface and/or a tapered bore. Swaging equipment used in such needle-suture attachment methods is also maintenance intensive.

Needle-suture attachment methods which have employed tubings heretofore also exhibit numerous disadvantages. Methods which employ metal tubings greatly diminish the flexibility of the needle-suture combination in the attachment region. Such diminished flexibility has a deleterious effect in many surgical procedures. Swaging of the tubing to the needle and the suture is also undesirable in that swaging is time-consuming, maintenance intensive, and subject to variability in attachment force.

Moreover, needle-suture attachment methods which have employed tubings heretofore have necessarily required the use of tubing having an inner diameter essentially equal to the outer diameters of the needle shank and suture tip to be attached. Too large a difference between the aforesaid inner and outer diameters inhibits the attachment process, and prevents a tight, secure interface between needle (and/or suture) and tubing. The limited tolerance between the tubing inner diameter and the needle shank/suture outer diameters in such methods make these dimensions critical, thereby making the attachment process more difficult and time-consuming, and increasing the likelihood of attachment failure and/or rejected materials.

In addition to the needle-suture constructions of the aforedescribed pull-out variety, it is known from U.S. Pat. No. 4,805,292 to provide a needle-suture combination in which a suture cutting edge is formed at the shank end of the needle. However, the combined needle-suture device of U.S. Pat. No. 4,805,292, like others described above, possesses a suture tip-receiving axial bore, or recess, formed in the butt end of the needle and as such is subject to the disadvantages recounted above which are associated with a needle possessing an axial bore.

SUMMARY OF THE INVENTION

In accordance with the present invention, there is provided a method for attaching a surgical needle to a suture to provide a combined surgical needle-suture device possessing an integrated suture cut-off feature which comprises:

(a) providing a needle possessing a shank end of reduced cross-section;

(b) placing a shrinkable tubing possessing a suture cutting edge around the reduced diameter shank and the suture such that in the combined surgical needle-suture device, the suture can be made to bear against the cutting edge of the tubing and be cut thereon thereby effecting separation of the needle from the suture; and, (c) applying energy to the shrinkable tubing to bring the tubing into engagement with the needle shank and suture.

In addition to the foregoing surgical needle-suture attachment method, the present invention includes the resulting combined surgical needle-suture device.

BRIEF DESCRIPTION OF THE DRAWINGS

The present invention will become more apparent from the following detailed description taken in conjunction with the accompanying drawings in which.

DETAILED DESCRIPTION OF THE INVENTION

Figure 4:
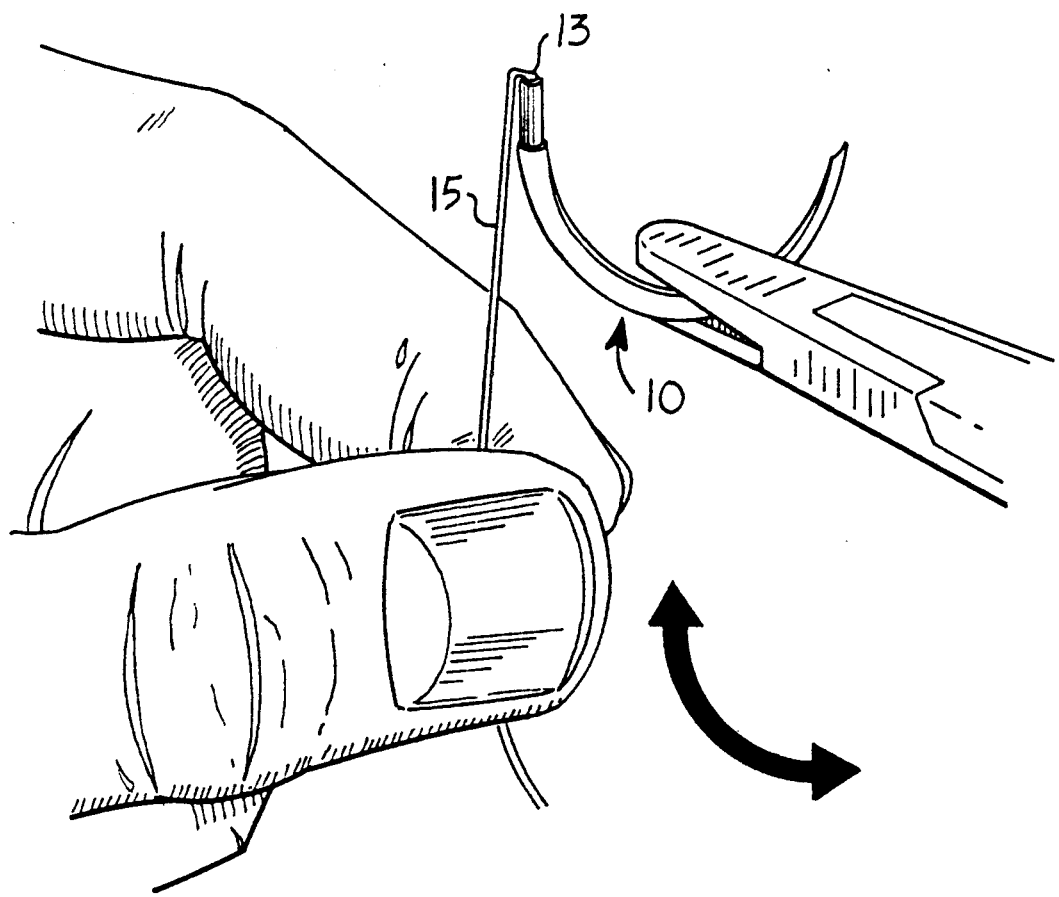
FIG. 4 illustrates the technique used in severing the suture from the needle.

The present invention relates to a combined surgical needle-suture method and resulting surgical needle-suture device which provides for separation of the suture from the needle by a quick, sharp lateral movement of the suture against the cutting edge of the tubular connector which has been employed to effect attachment of the needle to the suture as shown in FIG. 4. The invention has application to any suture material whether absorbable or non-absorbable, natural or synthetic, braided or monofilament, and to any needle material and configuration whether straight or curved.

Figure 1:
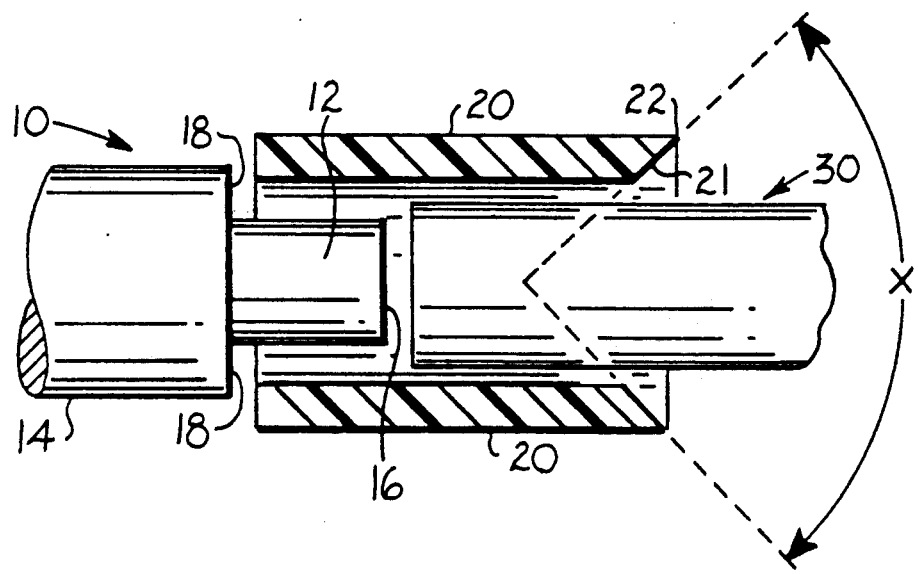
FIG. 1 is a side cross-sectional view of a needle and a suture with a tubing possessing a suture cutting edge positioned therearound (prior to engagement of the tubing with the needle and suture)
Figure 2:
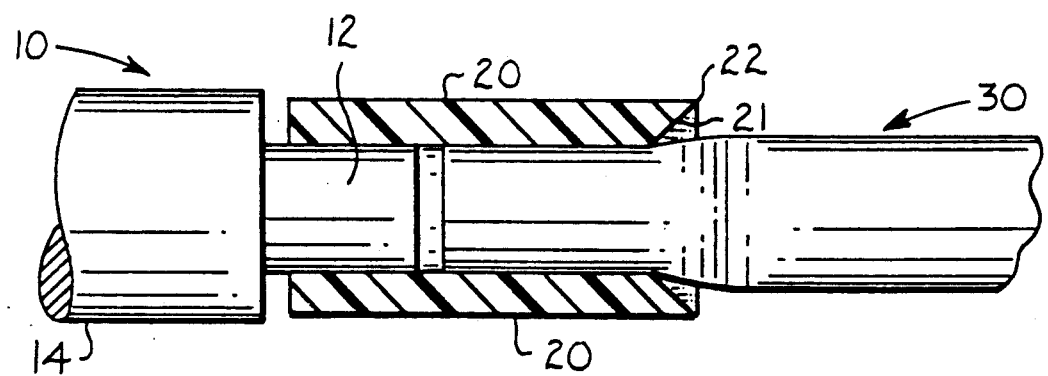
FIGS. 2 is a side cross-sectional view of the tubing of FIG. 1 in engagement with the needle and suture.
Figure 3:
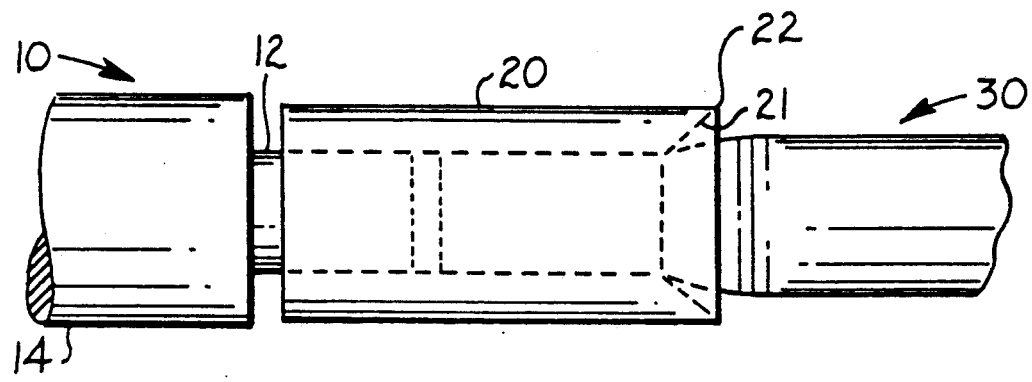
FIG. 3 is a side view of the combined surgical needle-suture device of FIG. 2.
Figure 5:
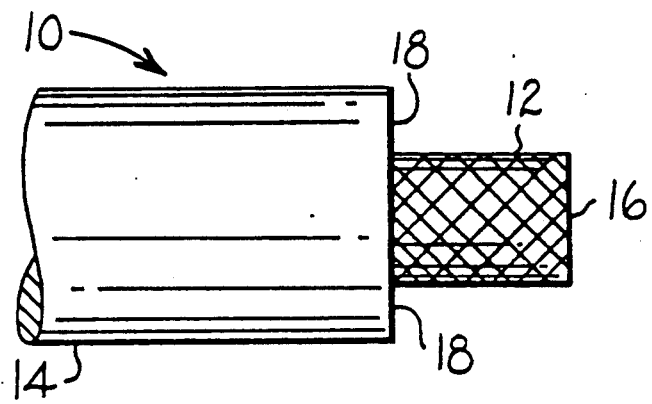
FIG. 5 is a side view of an alternative embodiment of the present invention in which a shank of the needle is scored.
Figure 6:
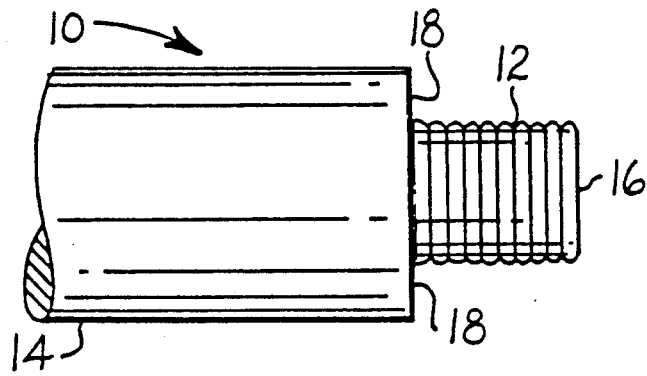
FIG. 6 is a side view of an alternative embodiment of the present invention in which the needle shank is ribbed.
Figure 7:
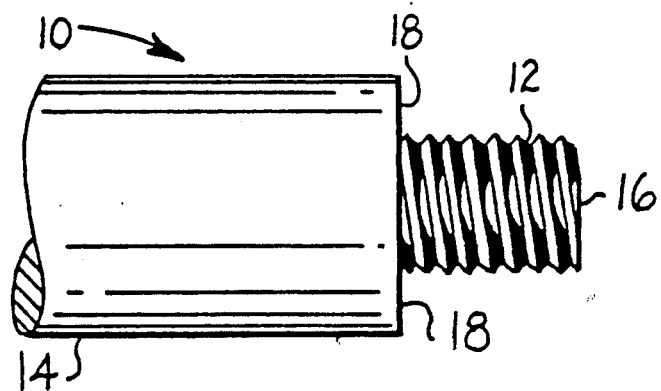
FIG. 7 is a side view of an alternative embodiment of the present invention in which the needle shank is threaded.
Figure 8:
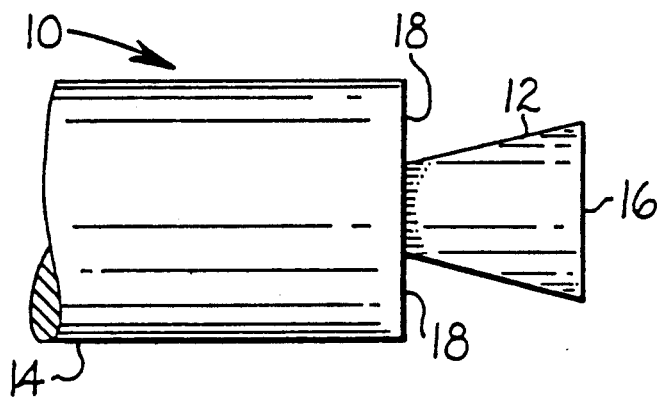
FIG. 8 is a side view of an alternative embodiment of the present invention in which the needle shank is tapered to expand in a direction away from a remainder of the needle.
Figure 9:
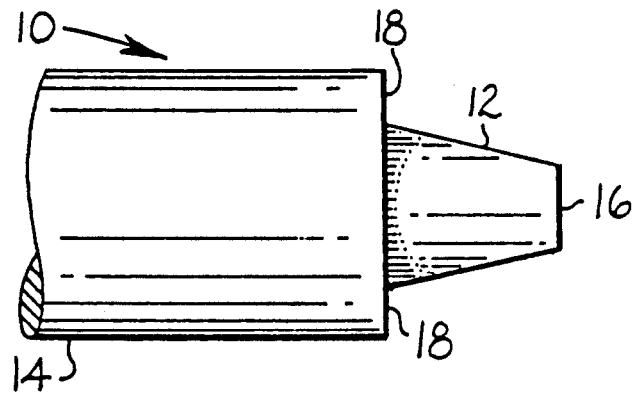
FIG. 9 is a side view of an alternative embodiment of the present invention in which the needle shank is tapered to expand in a direction towards the remainder of the needle.

Referring to FIGS. 1-3, needle 10 has a reduced cross-sectional diameter at its shank end 12 relative to the remaining portion 14 of the needle. The diameter of shank end 12 can be reduced by any conventional means, e.g., by machining on a lathe. Typically, shank end 12 has a diameter from 10 to 65% smaller than the remaining portion 14 of the needle and preferably from 25 to 50% smaller. It is also possible to provide shank end 12 with a texturized surface to facilitate gripping by shrinkable tubing 20. For example, shank end 12 may be scored, ribbed or threaded, in whole or in part (FIGS. 5-7 respectively). It may also be desirable to taper shank end 12 such that its butt, or distal end, 16 is of greater cross-sectional diameter than the cross-sectional diameter of shank end 12 in the region of shoulder 18, or vice versa (FIGS. 8 and 9 respectively). Shank end 12 is placed within tubing 20 as shown in FIG. 1.

Suture 30 is also positioned within shrinkable tubing 20 with suture tip 31 abutting or separated a short distance from distal end 16 of shank 12. As shown in FIG. 1, suture 30 may initially be of uniform cross-section throughout its length. Alternatively, the tip region of suture 30, i.e., the region inserted into tubing 20, may be of reduced cross-section relative to the remainder of suture 30, e.g., by tipping the suture tip with an adhesive or resinous tipping agent while suture 30 is under tension. (See, e.g., Canadian Pat. No. 1,009,532). Resin tipping may be desirable to prevent brooming of the suture, particularly for multifilament braided sutures, by rigidifying the end of the suture thus facilitating its handling during the attachment process. Reducing the diameter of the suture tip, as by tipping under tension, may be desirable to allow a suture of larger diameter, e.g., a suture diameter equal to the diameter of the needle to which it is to be attached, to be more efficiently attached to the needle using the shrinkable tubing of the present invention. It is not necessary according to the present invention, however, to reduce the diameter of the tip region of suture 30 to efficiently attach needle 10 to suture 30. Indeed, it may be possible or desirable to apply a tipping agent to prevent brooming without reducing suture diameter. As shown in FIG. 1, shrinkable tubing 20 initially has an inner diameter that is larger than the outer diameter of the tip region of suture 30, thereby minimizing the importance of suture tipping.

As shown in FIG. 1, the rear portion of shrinkable tubing 20 possesses a sloping surface 21 which terminates in a circumferential cutting edge 22 defined by an inclusive angle X formed at the junction of opposed sloped surfaces. The circumferential cutting edge can be smooth as shown or it can be notched or serrated to enhance or facilitate its cutting action. Aforesaid angle X which defines the slope of surface 21 of cutting edge 22 of tubing 20 is advantageously within some predetermined optimum range. On the one hand, if the value for inclusive angle X is below a certain minimum (which depends upon the structural/mechanical properties of the material from which the shrinkable tubing is fabricated and can be readily determined in a given case by simple and routine testing), the slope of surface 21 may be too steep for the tubing material to withstand the force of the tensioned cutting movement which is employed in severing suture 30 upon circumferential cutting edge 22. If, on the other hand, the value for inclusive angle X exceeds a certain maximum (again, as in the case of the minimum value of X, a variable which depends some extent upon the nature of the material from which tubing 20 is fabricated and readily determined for a specific tubing material by simple, routine testing), the slope may be too shallow to provide an effective cutting edge. For the tubings manufactured from any of the so-called "memory metals" identified below, the value of inclusive angle X is advantageously on the order of from about 90° to about 110° and is preferably from about 95° to about 105°.

It is, of course, necessary that the material from which tubing 20 is fabricated be capable of shrinking or undergoing contraction upon application of energy, e.g., heat, thereto but also of receiving a sharp cutting edge and holding the edge until such time as effective separation of the needle from its attached suture is desired. Suitable materials for construction of tubing 20 include "memory metals," e.g., nickel-titanium mixtures, or copper based materials, as are well known in the art (see, e.g., U.S. Pat. Nos. 3,759,552, 3,801,954, 4,198,081 and 4,733,680) available from Raychem Corporation, Menlo Park, Calif.

Cutting edge 22 and its associated sloping surface 21 can be formed on tubing 20 before or after the tubing has been attached to shank end 12 of needle 10 employing known or conventional machining techniques. It is particularly advantageous to form the cutting edge after the tubing has been attached to needle 10 but before attachment of suture 30 employing the apparatus and technique described in commonly assigned copending U.S. patent application Ser. No. 317,949, filed Mar. 2, 1989, now U.S. Pat. No. 4,984,941, the contents of which are incorporated by reference herein.

After shrinkable tubing 20 has been placed around shank end 12 of needle 10 and the tip region of suture 30 and after the machining operation providing cutting edge 22 has been carried out upon tubing 20, energy is applied to tubing 20. In response to this energy, tubing 20 shrinks or contracts thereby engaging shank end 12 of the needle and the tip region of suture 30. The overall length of tubing 20 may also be affected by the application of energy, e.g., the length of tubing 20 may reduce. Suitable energy sources for shrinking tubing 20 include heat (convective or conductive), radiation, microwave energy, etc.

As shown in FIGS. 1-2, shrinkable tubing 20 is simultaneously placed around both suture 30 and shank end 12 of needle 10 in one embodiment of the present invention. It is preferable, however, to sequentially secure tubing 20 to needle 10 and suture 30. Thus, in a preferred embodiment of the present invention, shrinkable tubing 20 is initially secured to shank end 12 through the localized application of energy to tubing 20 in the region surrounding shank end 12. After tubing 20 has been brought into engagement with shank end 12, the tip region of suture 30 is inserted into tubing 20 and additional energy is applied thereto Sequential shrinkage of tubing 20 makes it possible to vary the amount of energy used in securing tubing 20 to shank end 12 and suture 30, respectively, and to limit the exposure of suture 30 to energy during the attachment process. It may also be desirable to cool suture 30 in the region outside tubing 20 to prevent any undesirable degradation thereof, e.g., with a cold air curtain.

As shown in FIGS. 2-4, the shrinkage of tubing 20 typically compresses the tip region of suture 30 to some extent. This is particularly true where the suture is a braided, multi-filament material having void spaces in its structure. For example, tubing 20 may compress the tip region of suture 30 by as much as 30 to 35% for a braided, synthetic absorbable suture and by a minimal amount for a relatively stiff material such as a monofilament surgical gut.

The amount of energy applied to the tubing to effect the desired attachment, i.e., diameter reduction, depends upon the characteristics of the tubing material, the relative dimensions of the tubing, the shank end of the needle and the suture and the desired pull-out force for the needle-suture combination. Tubing 20 can be heated through contact with a hot gas stream or with heated dies or by other suitable heating means. Typically, the outer diameters of shank end 12 and the tip region of suture 30 are greater than the fully recovered diameter of tubing 20 such that tubing 20 engages shank end 12 and the tip region of suture 30. It is preferred that the attachment conditions be controlled such that the tubing remains secured to the needle once the suture is detached The foregoing surgical needle-suture attachment procedure has many advantages over previous attachment methods. Machining of the needle to provide a reduced diameter needle shank is much easier and more controllable than drilling processes, and permits the use of needle alloys which have previously been impractical, e.g., Series 300 stainless steel and MP35N (available from SPS Technologies). These heretofore impractical alloys have advantageous strength and ductility characteristics as compared to conventionally used Series 400 stainless steels. Moreover, an unreliable, expensive and maintenance intensive swaging process is replaced by a sterile, controllable and relatively inexpensive energy supply.

The attachment method is also much more efficient from a processing and inventory control standpoint. For example, the tubing may be removed from a needle and the needle attached to a fresh suture, e.g., in instances where the suture and/or attachment properties of the initial suture-needle combination are outside specifications. In many instances, the suture may also be recovered and reused, thereby greatly reducing processing waste. The range of acceptable suture diameters is greatly expanded due to the ability of the tubing to recover or shrink to varying degrees, thereby minimizing the likelihood that suture production will be rejected for inability to attach several needle sizes because the shrinkable tubing is capable of recovering or shrinking to varying degrees. This greatly simplifies inventory considerations. Moreover, the needle-suture combinations are atraumatic and advantageously exhibit flexibility in the attachment region.

While the combined surgical needle-suture device of FIG. 3 is in use, suture 30 will ordinarily avoid contact with circumferential cutting edge 22 of tubing 20. Occasional, unintentional and non-tensioned contact of the suture with cutting edge 22 will not affect the integrity of the surgical needle-suture combination. However, upon completion of suturing when separation of the surgical needle from the suture is desired, a deliberate arc-like, or sweeping, movement applied to the tensioned suture generally in the direction indicated by the arrow in FIG. 4 will be sufficient to sever the suture against circumferential cutting edge 22. Depending upon the size of the suture, an amount of force on the order of from about 3 oz. to about 4.0 lb., and preferably from about 6 oz. to about 2.5 lb., and one or just a few back-and-forth sweeps of the suture against cutting edge 22 will be effective to accomplish suture cut-off.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A method for attaching a surgical needle to a suture to provide a combined surgical needle-suture device possessing an integrated suture cut-off feature which comprises:
    (a) providing a needle possessing a shank end of reduced cross-section;
    (b) placing a shrinkable tubing possessing a suture cutting edge around the reduced diameter shank and the suture such that in the combined surgical needle-suture device, the suture can be made to bear against the cutting edge of the tubing and be cut thereon thereby effecting separation of the needle from the suture; and,
    (c) applying energy to the shrinkable tubing to bring the tubing into engagement with the needle shank and suture.

2. The method of claim 1 wherein the cutting edge is provided on the rear circumferential edge of the tubing, the cutting edge defining an inwardly sloping surface.

3. The method of claim 2 wherein the sloping surface defines an inclusive angle X having a value of from about 90° to about 110°.

4. The method of claim 2 wherein the sloping surface defines an inclusive angle X having a value of from about 95° to about 105°.

5. The method of claim 1 wherein the tubing is fabricated from a memory metal.

6. A combined surgical needle-suture device possessing an integrated suture cut-off feature which comprises:
    (a) a needle possessing a shank end of reduced cross section;
    (b) a suture possessing a tip abutting or proximate to the shank end of the needle; and,
    (c) a tubing fabricated from a shrinkable material and possessing a suture cutting edge on its rear edge, the front of the tubing engaging the shank end of the needle and the rear of tubing engaging the tip of the suture such that attachment of the needle to the tubing is effected.

7. The combined surgical needle-suture device of claim 6 wherein the cutting edge is provided on the rear circumferential edge of the tubing, the cutting edge defining an inwardly sloping surface.

8. The combined surgical needle-suture device of claim 7 wherein the sloping surface defines an inclusive angle X having a value of from about 90° to about 110°.

9. The combined surgical needle-suture device of claim 7 wherein the sloping surface defines an inclusive angle X having a value of from about 95° to about 105°.

10. The combined surgical needle-suture device of claim 6 wherein the tubing is fabricated from a memory metal.

11. The combined surgical needle-suture device of claim 6 wherein the shank end is provided with a texturized surface to facilitate gripping by said shrinkable tubing.

12. The combined surgical needle-suture device of claim 11 wherein the shank end is scored, ribbed or threaded, in whole or in part.

13. The combined surgical needle-suture device of claim 6 wherein said shank end of reduced cross section forms a shoulder with a remainder of said needle.

14. The combined surgical needle-suture device of claim 13 wherein said shank of reduced cross section is tapered to expand in a direction away from said shoulder, such that a distal end of said shank end is of greater cross-sectional diameter than cross-sectional diameter of said shank end in a region of said shoulder.

15. The combined surgical needle-suture device of claim 13 wherein said shank end of reduced cross-section is tapered to expand in a direction toward said shoulder, such that a distal end of said shank end is of smaller cross-sectional diameter than cross-sectional diameter of said shank end in a region of said shoulder.

* * * * *

UNITED STATES PATENT AND TRADEMARK OFFICE
CERTIFICATE OF CORRECTION

PATENT NO.  : 5,041,128

DATED       : August 20, 1991

INVENTOR(S) : Herbert W. Korthoff

It is certified that error appears in the above-identified patent and that said Letters Patent is hereby corrected as shown below:

On the Title Page, delete line [73] and substitute the following:

-- [73]  Assignee:  United States Surgical Corporation, Norwalk, Conn. --;

Column 2, line 64 of the specification, delete "b".

Signed and Sealed this

Thirteenth Day of October, 1992

Attest:

DOUGLAS B. COMER

Attesting Officer

Acting Commissioner of Patents and Trademarks